United States Patent [19]

Kolts

[11] Patent Number: 4,579,997
[45] Date of Patent: Apr. 1, 1986

[54] OLEFIN PRODUCTION OVER CATALYTIC OXIDES OF MN AND AT LEAST ONE OF NB AND A LANTHANIDE

[75] Inventor: John H. Kolts, Ochelata, Okla.

[73] Assignee: Phillips Petroleum Company, Bartlesville, Okla.

[21] Appl. No.: 758,937

[22] Filed: Jul. 25, 1985

[51] Int. Cl.$^4$ .............................................. C07C 4/02
[52] U.S. Cl. ................... 585/653; 585/651; 585/661
[58] Field of Search ....................... 585/651, 653, 661

[56] References Cited

U.S. PATENT DOCUMENTS

| | | | |
|---|---|---|---|
| 2,415,477 | 2/1947 | Folkins et al. | 585/651 |
| 3,644,557 | 2/1972 | Senes et al. | 585/651 |
| 3,751,514 | 8/1973 | Hoppstock et al. | 585/653 |
| 3,751,516 | 8/1973 | Frech et al. | 585/653 |
| 3,766,278 | 10/1973 | Bogart et al. | 585/651 |
| 4,087,350 | 5/1978 | Kolombos et al. | 585/653 |
| 4,093,536 | 6/1978 | Heckelsberg | 585/653 |
| 4,152,300 | 5/1979 | Riesser | 502/324 |
| 4,159,970 | 7/1979 | Heckelsberg | 502/324 |
| 4,471,151 | 9/1984 | Kolts | 585/651 |

FOREIGN PATENT DOCUMENTS

| | | | |
|---|---|---|---|
| 47-42703 | 12/1972 | Japan | 585/653 |
| 1306087 | 2/1973 | United Kingdom | 585/651 |
| 0422165 | 8/1974 | U.S.S.R. | 585/651 |
| 0626111 | 9/1978 | U.S.S.R. | 585/651 |

Primary Examiner—John Doll
Assistant Examiner—Lance Johnson
Attorney, Agent, or Firm—C. F. Steininger

[57] ABSTRACT

Compositions of matter, including: A mixture of at least one oxide of manganese and at least one oxide of a Lanthanum Series metal, preferably lanthanum or cerium, or at least one oxide of niobium. The above compositions are particularly useful as catalytic compositions for the conversion of $C_3$ and $C_4$ hydrocarbons to less saturated hydrocarbons, particularly ethylene and propylene and preferably ethylene. The life of the catalyst for the selective production of ethylene is extended by carrying out the reaction in the presence of steam. The steam substantially increases the active life of the catalytic composition, before regeneration is necessary, as well as significantly increasing the selectivity to ethylene. Limiting the amount of "bound" or "fixed" sulfur in the catalytic composition also improves the catalyst.

12 Claims, No Drawings

OLEFIN PRODUCTION OVER CATALYTIC OXIDES OF MN AND AT LEAST ONE OF NB AND A LANTHANIDE

The present invention relates to improved compositions of matter. In a more specific aspect, the present invention relates to improved catalysts for the conversion of $C_3$ and $C_4$ hydrocarbons to less saturated hydrocarbons. In a more specific aspect, the present invention relates to improved catalysts for the conversion of $C_3$ and $C_4$ alkanes to less saturated hydrocarbons, particularly ethylene and propylene and preferably ethylene.

BACKGROUND OF THE INVENTION

Olefins, such as ethylene and propylene, have become major feedstocks in the organic chemical and petrochemical industries. Of these, ethylene is by far the most important chemical feedstock, since the requirements for ethylene feedstocks are about double those for propylene feedstocks. Consequently, improved methods for the conversion of less valuable hydrocarbons to ethylene and propylene, and particularly to ethylene, are highly desirable.

Numerous suggestions have been made for the production of ethylene and propylene, particularly ethylene, from various feedstocks and by a wide variety of processes.

At the present time ethylene is produced almost exclusively by dehydrogenation or thermal cracking of ethane and propane, naphtha and, in some instances, gas oils. About 75% of the ethylene currently produced in the United States is produced by steam cracking of ethane and higher normally gaseous hydrocarbon components of natural gas, since natural gas contains from about 5 vol.% to about 60 vol.% of hydrocarbons other than methane. However, in most instances, the content of ethane and higher normally gaseous hydrocarbon materials in natural gas is less than about 25% and usually less than about 15%. Consequently, these limited quantities of feedstocks, which are available for the production of ethylene and propylene, and particularly etheylene, must be utilized efficiently. Unfortunately, these processes result in low conversions to olefins and selectivity to ethylene, as opposed in propylene, is poor. In addition, relatively severe conditions, particularly temperatures in excess of about 1000° C., are required and such processes are highly energy intensive.

In order to reduce the severity of the conditions and, more importantly, to improve the conversion of normally gaseous feedstocks to ethylene and propylene and selectivity to ethylene, numerous processes involving the use of solid contact materials have been proposed. Some of these proposals utilize inert solid contact materials to improve contact between the feed hydrocarbons and steam and also to maintain a more even temperature throughout the zone of reaction. In other instances, the solid contact material is catalytic in nature. Such use of solid contact materials, particularly catalysts, have resulted in modest improvements in conversion to ethylene and propylene but the selectivity to ethylene is improved very little. It is, therefore, highly desirable that improved catalytic processes be developed, particularly processes which increase the selectivity to ethylene, as opposed to propylene. However, little is understood concerning the manner in which such catalysts function, why certain components are effective while similar components are ineffective, or why certain combinations of components are effective and other combinations are not. Obviously, a number of theories have been proposed by workers of the art, but this only adds to the confusion, since it appears that each theory explains why a particular catalytic material works well, but does not explain why similar catalytic materials do not work and why other dissimilar materials are effective. As a result, the art of catalytic conversion of hydrocarbons to olefins remains highly unpredictable.

SUMMARY OF THE INVENTION

It is therefore an object of the present invention to provide improved compositions of matter and methods of utilizing the same, which overcome the above and other disadvantages of the prior art. Another object of the present invention is to provide improved compositions of matter. Still another object of the present invention is to provide improved catalytic compositions for the conversion of $C_3$ and $C_4$ hydrocarbons to less saturated hydrocarbons. Another and further object of the present invention is to provide an improved method for the conversion of $C_3$ and $C_4$ hydrocarbons to less saturated hydrocarbons, preferably in the presence of steam. Yet another object of the present invention is to provide an improved process for the conversion of $C_3$ and $C_4$ hydrocarbons to less saturated hydrocarbons, in the presence of steam, to selectively produce ehtylene, ethane and propylene, and particularly ethylene. A further object of the present invention is to provide an improved catalytic material for the conversion of $C_3$ and $C_4$ hydrocarbons to less saturated hydrocarbons, which has an improved effective life, before regeneration is necessary, particularly for the production of ethylene, ethane and propylene, and more particularly ethylene.

The present invention provides improved compositions of matter, including mixed oxides of manganese and at least one metal selected from the group consisting of Lanthanum Series metals and niobium. Preferred Lanthanum Series metals are selected from the group consisting of lanthanum and cerium. These compositions of matter have been found to be highly effective catalyst compositions for the conversion of feed hydrocarbons comprising at least one of $C_3$ and $C_4$ hydrocarbons to less saturated hydrocarbons. A method of converting feed hydrocarbons comprising $C_3$ and $C_4$ hydrocarbons to less saturated hydrocarbons, particularly ethylene and propylene and preferably ethylene, is provided in which the feed hydrocarbons are contacted with one of the above-mentioned catalytic compositions, preferably in the presence of steam, under conditions sufficient to convert the feed hydrocarbons to less saturated hydrocarbons.

DETAILED DESCRIPTION OF THE INVENTION

The hydrocarbon feed components, in accordance with the present invention, can include any normally gaseous hydrocarbon stream containing significant amounts of $C_3$ and $C_4$ hydrocarbons, particularly propane and n-butane, with n-butane being preferred. The presence of other normally gaseous components or even normally liquid components, which vaporize at operating conditions, are not detrimental to the process. For example, it has been found that if isobutane is utilized, in accordance with the present invention, the catalysts of the present invention shift the product stream from isobutene to propylene and, therefore, one of the desired products of the present invention is produced. On the other hand, it has been found that the catalytic process of the present invention is generally ineffective, as compared with a strictly thermal process, in improving the conversion of ethane to ethylene. However, the presence of ethane in feed hydrocarbons, obviously, is not detrimental. Components other than hydrocarbons are also not detrimental. The primary criteria in all cases is the cost or difficulty of separating inert materials or the products of components other than $C_3$ and $C_4$ hydrocarbons from the desired ethylene and propylene and whether such separation is less costly and/or less difficult before or after conduct of the process of the present invention. Suitable feedstocks for the process of the present invention can be obtained from any source, including natural gas, refinery off-gases and the like. However, the most convenient and abundant source is $C_3$ and $C_4$ hydrocarbon streams recovered during the processing of a natural gas to produce a pipeline gas for heating purposes. Conventionally, $C_2$ and higher hydrocarbons are separated from methane to produce a pipeline gas for heating purposes, which predominates in methane, by compression and expansion, cryogenic means or a combination of both. Usually, the natural gas, either at a high pressure as produced or compressed to a high pressure, is treated to successively condense first normally liquid hydrocarbons ($C_6+$ hydrocarbons or natural gasoline), then $C_5$, followed by $C_4$, then $C_3$ and, finally, $C_2$ hydrocarbons, by cooling to successively lower temperatures with the separation or fractionation of the condensed liquid from uncondensed vapor between cooling stages. Thus, individual streams predominating in an individual hydrocarbon, such as $C_5$, $C_4$, $C_3$ and $C_2$, can be obtained or streams predominating in combinations of the individual hydrocarbons can be recovered. Accordingly, the thus separated propane stream or the thus separated butanes stream can be utilized as a feed hydrocarbon for the present invention, or a stream predominating in a mixture of propane and butanes can be utilized. Obviously, the latter would eliminate the necessity of one stage of cooling and separation in a natural gas processing system.

The compositions of matter of the present invention include: a composition comprising at least one oxide of manganese and at least one oxide of a metal of the Lanthanum Series, preferably lanthanum or cerium, or niobium. From time to time herein, the manganese oxide is referred to as a promoter or active component and the Lanthanum Series oxide or niobium oxide as the base material. This reference is simply a matter of convenience, because the manganese oxide is usually the minor component and the Lanthanum Series oxide or the niobium oxide are major components. Accordingly, it is to be understood that such reference is not meant to categorize the components. As will appear hereinafter, all the recited components are necessary and are catalytically active in the process of the present invention.

The above-mentioned compositions of matter have been found to be particularly effective as catalytic compositions for the conversion of $C_3$ and $C_4$ hydrocarbons to less saturated hydrocarbons. Accordingly, for such use, the composition will generally contain from about 0.1 to about 30 wt. % of manganese, expressed in terms of elemental manganese based on the total weight of the composition, and preferably between 0.5 and about 15 wt. % manganese.

The method of preparation of the catalyst compositions of the present invention does not appear to be critical, so long as the desired final compositions of the component metal oxides are present. Suitable methods of preparation include slurry blending, solution blending, dry blending, impregnation and coprecipitation, all of which are well-known to those skilled in the art. A convenient method is to add metal solids, for example, $La_2O_3$, to a blending apparatus along with a solution of a metal salt, such as manganese nitrate, and mixing for several minutes, for example, 2–5 minutes, to form a thick slurry. In the interest of economy, excess water should be avoided. The resultant slurry is then dried in air by conventional means, at about 100° C. to 150° C., calcined for about 4 hours, at about 750° C. to 800° C., and then ground, sieved and, optionally, pelleted or otherwise sized by means well known to those skilled in the art.

During operation, in accordance with the present invention, it has been found that small amounts of the feed hydrocarbons are converted to coke, which is then deposited upon the catalyst and contributes to a decline in the activity of the catalyst, particularly the selectivity to ethylene. Accordingly, it is desirable to periodically regenerate the catalyst by conventional techniques of carbon removal, such as treatment with an oxygen-containing gas, such as air. During such regeneration, it may also be desirable to use inert gas or steam dilution to control burn-off temperatures, as is also well known to those skilled in the art. The catalysts of the present invention have been found to be particularly valuable, to the extent that they may be utilized for greatly extended periods of time for the production of olefins, particularly for the production of ethylene, without regeneration. In addition, it has been found that the presence of steam, during the conduct of the conversion of $C_3$ and $C_4$ hydrocarbons, also extends the effective life of the catalysts between regenerations. For example, it has been found that, without steam, catalysts which have been effective for the production of olefins, particularly ethylene, from $C_3$ and $C_4$ hydrocarbons, require regeneration to maintain high ethylene production rates. When steam is utilized, this period, before regeneration, is extended. However, as will be shown in the examples hereinafter, the catalysts of the present invention have greatly extended effective lives, before regeneration is necessary.

It is also highly desirable, in accordance with the present invention, to limit the amount of "bound" or "fixed" sulfur in the components used to prepare the catalysts of the present invention. It appears that the presence of such "bound" or "fixed" sulfur in the catalytic material tends to inhibit selectivity of the catalyst for the production of $C_2$ hydrocarbons. Such sulfur is referred to as "bound" or "fixed" sulfur, since it does not appear to be converted to hydrogen sulfide or to be otherwise lost during the hydrocarbon conversion process or the regeneration step and is probably present in sulfate form.

The process of the present invention can be carried out in fixed, moving, fluidized, ebullating or entrained bed reactors. For experimental purposes and, obviously, to permit accurate measurement and precise control of the process variables, the runs hereinafter set forth in the examples were conducted in a fixed bed reactor.

Following preparation of the catalytic composition, the catalyst may be prepared for use by purging with an inert gas, such as nitrogen. Normally, the catalyst would be disposed in the reactor and be brought up to reaction temperature by preheating with air, then purging with hot nitrogen and, finally, introducing the hydrocarbon feed. Since it is preferred that steam be added to the hydrocarbon feed, in the conduct of the process of the present invention, it may be preferred to use steam rather than nitrogen as a purging gas. The catalyst may also, optionally, be pretreated with hydrogen before use. Such treatment is preferably carried out at about the operating temperature of the process and at a pressure up to about 600 psia. Such hydrogen pretreatment appears to reduce higher oxidation states of manganese and, thereby, reduce initial carbon oxide formation.

With the exception of the the temperature of operation, the operating conditions of the process, in accordance with the present invention, do not appear to be highly critical. Accordingly, the following conditions of operation are those found effective and preferred.

When steam is utilized, the steam/hydrocarbon mol ratio may be between about 0.1/1 to about 10/1 and is preferably between about 0.5/1 and about 5/1.

The hydrocarbon gas hourly space velocity (GHSV) may range from about 100 to about 3000 but is preferably between about 500 and about 1000.

The operating pressure may be between about 0.1 to about 100 psia and is preferably between about 1 and about 60.

The temperature of operation appears to be significant in the conversion of feed hydrocarbons to olefins and particularly in improving the selectivity to ethylene. Suitable temperatures range between about 550° C. and about 850° C., with the preferred range being between about 650° C. and about 775° C.

The nature and advantages of the present invention are illustrated by the following examples.

EXAMPLE 1

Quartz chips were utilized for a comparative run representative of thermal cracking in the presence of steam. All catalysts, in general, were prepared either by incipient wetness impregnation of the support oxides or coprecipitation from various soluble materials. The 4% manganese on ceria was prepared by heating $CeO_2$ in water, at 60° C. to 100° C. for about 1–5 hours, before impregnating with the manganese. The 5% manganese on ceria was essentially dry $CeO_2$ impregnated with manganese. The promoting materials were in their oxide form, but their concentrations are reported as weight percent of elemental metal based on the total weight of the catalyst.

The reactor was a fixed bed 18 mm (i.d.) quartz reactor which held 25 cc of catalyst. The reactor contained a quartz thermocouple well centered axially along the catalyst bed and the temperatures reported are at the longitudinal midpoint in the catalyst bed. In the experiments reported, all catalysts were pretreated in the same manner. This pretreatment involved air oxidation for ten minutes, nitrogen purge for two minutes, hydrogen reduction for ten minutes and a final nitrogen purge. The catalyst was brought up to reaction temperature prior to the introduction of the hydrocarbon feed.

Effluent from the reactor was snap sampled and analyzed by chromatographic techniques. Product sampling was normally after 2 to 5 minutes of feed. This reaction time determines the "initial activity" of a catalyst. The conversion, as reported, is mole percent of n-butane converted and the selectivities are based on normalized moles of feed converted to the indicated products.

TABLE 1

| Catalyst | Temp. °C. | Conv. | Selectivity $C_2=$ | $C_3=$ | $C_2$ | $C_2=+C_2$ / $C_3=$ |
|---|---|---|---|---|---|---|
| Quartz Chips | 675 | 27 | 30 | 43 | 6 | 0.83 |
|  | 720 | 50 | 30 | 39 | 7 | 0.95 |
| 4% Mn/La$_2$O$_3$ | 660 | 50 | 27 | 24 | 21 | 2.00 |
| 2% Mn/La$_2$O$_3$ | 675 | 64 | 28 | 24 | 18 | 1.91 |
| 5% Re/La$_2$O$_3$ | 690 | 50 | 26 | 30 | 11 | 1.23 |
| 4% Mn/CeO$_2$ | 675 | 76 | 26 | 23 | 19 | 1.96 |
| 5% Mn/CeO$_2$ | 675 | 39 | 34 | 31 | 16 | 1.61 |
| 5% Mn/CeO$_2$ | 691 | 50 | 32 | 29 | 14 | 1.59 |
| 6% Mn/Nb$_2$O$_5$ | 700 | 50 | 31 | 29 | 9 | 1.69 |

While propylene is also a desirable product in accordance with the present invention, because of greater demands for ethylene the catalysts of the present invention and the conditions of operation are selected to increase the production of ethylene and decrease the production of propylene. Accordingly, the effectiveness of the catalysts is indicated by the ratio of ethylene plus ethane to propylene, since the ethane can be converted to additional ethylene. On this basis, it is to be observed from the above table that the thermal conversion results in an ethylene plus ethane to propylene ratio of 1.00 or less. The propylene production significantly exceeds the ethylene production. However, the catalysts of the present invention reverse this situation and it can be seen that catalysts, in accordance with the present invention, significantly increase the production of ethylene while decreasing the production of propylene and, most significantly, the ratio of ethylene plus ethane to propylene is generally above 1.00 and usually close to 2.00. Rhenium is often considered an alternative catalytic material to manganese. However, it was found to be little better than the quartz chips.

As previously pointed out, both components of the catalytic materials of the present invention are necessary to the selective production of ethylene, in accordance with the present invention. For example, similar runs were made using $La_2O_3$ and $CeO_2$ alone, as catalysts. In these runs, it was found that the results were essentially the same, within experimental error, as the thermal conversion.

As previously pointed out, the catalysts of the present invention have a greatly increased effective life, before regeneration is necessary. As a general rule, it is deemed that regeneration is necessary when the production of propylene equals or exceeds the production of ethylene. The following run was made in order to demonstrate this extended life of the catalysts of the present invention.

EXAMPLE 2

In this run a catalyst comprising 7% magnesium on lanthanum oxide was utilized to convert n-butane at 640° C. and utilizing a steam/feed hydrocarbon ratio of 1/1. Otherwise, the conditions and mode of operation were the same as those of the previous example.

TABLE 2

N—Butane Conversion Over 7% Mn/La$_2$O$_3$ at 640° C., 1/1 Steam/Hydrocarbon Ratio

| On-Stream Time, Min. | Conversion, % | Selectivity, % $C_2=$ | $C_3=$ | $C_2$ | $C_2=+C_2$ / $C_3=$ |
|---|---|---|---|---|---|
| 50 | 41 | 29 | 24 | 28 | 2.4 |
| 140 | 43 | 28 | 24 | 27 | 2.3 |
| 160 | 41 | 28 | 24 | 27 | 2.3 |
| 230 | 42 | 29 | 25 | 26 | 2.2 |
| 280 | 40 | 28 | 25 | 26 | 2.2 |

TABLE 2-continued

N—Butane Conversion Over 7% Mn/La$_2$O$_3$ at 640° C., 1/1 Steam/Hydrocarbon Ratio

| On-Stream Time, Min. | Conversion, % | Selectivity, % C$_2$= | C$_3$= | C$_2$ | C$_2$=+C$_2$ / C$_3$= |
|---|---|---|---|---|---|
| 360 | 41 | 28 | 25 | 26 | 2.2 |
| 400 | 40 | 28 | 25 | 26 | 2.2 |
| 470 | 42 | 28 | 25 | 26 | 2.2 |
| 560 | 42 | 28 | 25 | 26 | 2.2 |
| 600 | 36 | 29 | 26 | 24 | 2.0 |
| 660 | 34 | 28 | 27 | 21 | 1.8 |
| 1120 | 31 | 26 | 30 | 16 | 1.4 |
| 1600 | 25 | 24 | 42 | 10 | 0.8 |

As previously pointed out, a typical catalyst, for the selective conversion of C$_3$ and C$_4$ hydrocarbons to ethylene in the presence of steam, will require regeneration within about an hour, while such selective catalysts with additional promoters, adapted to extend the life thereof, may be utilized for periods up to four hours before regeneration. However, it is to be observed from the above Table that the catalysts of this invention can be utilized for a period of about 11 hours before regeneration is necessary.

Another series of runs was made in order to determine the effect of the amount of manganese on a La$_2$O$_3$ base.

EXAMPLE 3

In this series of runs n-butane was utilized as a feed hydrocarbon at 650° C. and at a steam/feed hydrocarbon ratio of 1/1. Other conditions were essentially the same as those previously utilized. In this series of runs, the effect of varying amounts of manganese is demonstrated.

TABLE 3

| % Mn on La$_2$O$_3$ | Conversion, % | Selectivity, % C$_2$= | C$_3$= | C$_2$ | C$_2$=+C$_2$ / C$_3$= |
|---|---|---|---|---|---|
| 0 | 30 | 22 | 41 | 9 | 0.76 |
| 0.25 | 22 | 27 | 36 | 14 | 1.14 |
| 0.60 | 30 | 27 | 33 | 16 | 1.30 |
| 1.0 | 42 | 27 | 30 | 19 | 1.53 |
| 2.0 | 44 | 28 | 27 | 20 | 1.78 |
| 4.0 | 44 | 27 | 24 | 21 | 2.00 |
| 7.0 | 67 | 21 | 16 | 22 | 2.69 |
| 10.0 | 74 | 18 | 14 | 20 | 2.71 |

The above data together with other data have shown that the useful range of the manganese, in the catalyst of the present invention, is from about 0.1 to about 30 wt. %, expressed in terms of elemental manganese based on the total weight of the catalyst, and preferably between about 0.5 and 7 wt. %.

EXAMPLE 4

Yet another series of runs was made comparing thermal conversion of n-butane (quartz chips) with a catalyst containing 5% manganese on CeO$_2$ at various temperatures within the range of the desirable temperatures of operation of the present invention.

The CeO$_2$ was heated in water at 60°–100° C. for about 1 to 5 hours before impregnation with Mn.

The conditions of operation were essentially the same as those previously utilized and including an n-butane feed rate of 100 cc/min at a 1/1 steam/feed hydrocarbon ratio.

TABLE 4

| Catalyst | Temp (°C.) | Conv. | Selectivity C$_2$= | C$_3$= | C$_2$ | C$_2$=+C$_2$ / C$_3$= |
|---|---|---|---|---|---|---|
| Quartz Chips | 643 | 19.0 | 25.1 | 46.1 | 8.5 | 0.73 |
| | 676 | 27.4 | 29.1 | 43.7 | 6.2 | 0.81 |
| | 697 | 52.8 | 29.7 | 39.1 | 7.8 | 0.96 |
| 5% Mn/CeO$_2$ | 627 | 16.9 | 31.8 | 31.4 | 21.3 | 1.69 |
| | 659 | 29.7 | 31.8 | 32.0 | 17.2 | 1.53 |
| | 686 | 44.3 | 34.0 | 29.8 | 15.6 | 1.66 |
| | 708 | 59.8 | 34.3 | 28.0 | 13.3 | 1.66 |

It can be seen from the above that conversion, in the presence of the catalyst of the present invention, is significantly higher at comparable temperatures and, more importantly, the selectivity to ethylene plus ethane, as opposed to propylene, is substantially improved.

The effect of the presence or absence of steam during the conduct of the present invention is illustrated by the following example.

EXAMPLE 5

In this example a catalyst comprising 4% manganese on CeO$_2$ was prepared from CeO$_2$ which had been heated in water, as previously indicated, and, thereafter, impregnated with manganese. Conditions were essentially the same as those previously utilized, including a steam/feed hydrocarbon ratio of 1/1, n-butane as a feed and a temperature of 665° C.

TABLE 5

| Co-Feed | Time Min. | Conversion | Selectivity C$_2$= | C$_3$= | C$_2$ | C$_2$=+C$_2$ / C$_3$= |
|---|---|---|---|---|---|---|
| N$_2$ | 3 | 54.8 | 27.6 | 28.3 | 16.1 | 1.54 |
| | 40 | 38.1 | 24.9 | 43.3 | 8.7 | 0.78 |
| Steam | 3 | 67.6 | 25.9 | 25.7 | 19.6 | 1.77 |
| | 44 | 65.4 | 27.2 | 25.6 | 19.7 | 1.83 |

As can be seen from the above data, the catalyst of the present invention showed no loss in activity after about forty minutes on stream. However, where steam was absent, virtually all catalytic activity was lost after about forty minutes.

While specific materials, conditions of operations, modes of operation and equipment have been referred to herein, it is to be recognized that these and other specific recitals are for illustrative purposes and to set forth the best mode only and are not to be considered limiting.

I claim:

1. A method for converting feed hydrocarbons comprising at least one of C$_3$ and C$_4$ hydrocarbons to less saturated product hydrocarbons, comprising:
   contacting said feed hydrocarbons with a catalyst composition comprising:
   (a) at least one oxide of manganese and
   (b) at least one oxide of at least one metal selected from the group consisting of Lanthanum Series metals and niobium,
   under conditions sufficient to convert said feed hydrocarbons to said less saturated product hydrocarbons.

2. A method in accordance with claim 1 wherein the feed hydrocarbons comprise propane.

3. A method in accordance with claim 1 wherein the feed hydrocarbons comprise butanes.

4. A method in accordance with claim 1 wherein the feed hydrocarbons comprise a mixture of propane and butanes.

5. A method in accordance with claim 1 wherein the conditions are sufficient to selectively convert the feed hydrocarbons to ethylene and ethane.

6. A method in accordance with 5 wherein the conditions are sufficient to selectively convert the feed hydrocarbons to ethylene.

7. A method in accordance with claim 1 wherein the metal selected from the group consisting of Lanthanum Series metals and niobium is a metal selected from the group consisting of Lanthanum Series metals.

8. A method in accordance with claim 7 wherein the metal selected from the group consisting of Lanthanum Series metals is a metal selected from the group consisting of lanthanum and cerium.

9. A method in accordance with claim 1 wherein the manganese is present in an amount between about 0.1 and about 30 wt. %, expressed in terms of elemental manganese based on the total weight of the catalyst.

10. A method in accordance with claim 1 wherein the temperature is maintained between about 550° C. and about 850° C.

11. A method in accordance with claim 1 wherein the contacting is carried out in the presence of steam at a steam/feed hydrocarbon mol ratio between about 0.1/1 and about 10/1.

12. A method in accordance with claim 1 wherein the sulfur content of the catalyst composition is below about 0.2 wt. %, expressed in terms of elemental sulfur based on the total weight of said catalyst.

* * * * *